US006620586B2

(12) United States Patent
Dattagupta

(10) Patent No.: US 6,620,586 B2
(45) Date of Patent: Sep. 16, 2003

(54) METHODS AND COMPOSITIONS FOR ANALYZING NUCLEIC ACIDS

(75) Inventor: Nanibhushan Dattagupta, San Diego, CA (US)

(73) Assignee: Applied Gene Technologies, Inc., San Diego, CA (US)

( * ) Notice: Subject to any disclaimer, the term of this patent is extended or adjusted under 35 U.S.C. 154(b) by 0 days.

(21) Appl. No.: 09/791,030

(22) Filed: Feb. 20, 2001

(65) Prior Publication Data

US 2002/0115074 A1 Aug. 22, 2002

(51) Int. Cl.$^7$ .................................................. C12Q 1/68
(52) U.S. Cl. .............................. 435/6; 435/6; 435/91.2; 536/22.1; 536/23.1; 536/24.3; 536/24.31
(58) Field of Search .................. 435/6, 91.2; 536/22.1, 536/23.1, 24.3, 24.31, 24.32, 24.33

(56) References Cited

U.S. PATENT DOCUMENTS

| | | | |
|---|---|---|---|
| 4,683,195 A | 7/1987 | Mullis et al. ................... 435/6 |
| 4,683,202 A | 7/1987 | Mullis ......................... 435/91 |
| 4,734,454 A | 3/1988 | Aihara et al. ............... 524/555 |
| 4,838,697 A | 6/1989 | Kurandt ..................... 356/406 |
| 5,026,840 A | 6/1991 | Dattagupta et al. ........... 536/27 |
| 5,139,940 A | 8/1992 | Isaacs et al. ................. 435/91 |
| 5,409,818 A | 4/1995 | Davey et al. ............. 435/91.21 |
| 5,498,279 A | 3/1996 | Klemp ........................ 96/104 |
| 5,554,517 A | 9/1996 | Davey et al. ............. 435/91.21 |
| 5,736,330 A | 4/1998 | Fulton ........................... 435/6 |
| 5,802,327 A | 9/1998 | Hawley et al. ............. 395/281 |
| 5,850,479 A | 12/1998 | Terry et al. ................. 382/211 |
| 5,981,180 A * | 11/1999 | Chandler et al. ............... 435/6 |
| 6,046,807 A | 4/2000 | Chandler .................... 356/318 |
| 6,057,107 A | 5/2000 | Fulton .......................... 435/6 |
| 6,139,800 A * | 10/2000 | Chandler ................. 422/82.08 |
| 6,148,658 A | 11/2000 | Chou ....................... 73/24.01 |
| 6,165,800 A * | 12/2000 | Jiang et al. ................. 435/546 |
| 6,187,566 B1 * | 2/2001 | Dattagupta et al. ........ 435/91.1 |
| 6,242,188 B1 * | 6/2001 | Dattagupta et al. ............ 435/6 |

FOREIGN PATENT DOCUMENTS

| | | |
|---|---|---|
| WO | WO 90 12020 | 10/1990 |
| WO | WO 91 02735 | 3/1991 |
| WO | WO 00 53809 | 9/2000 |

OTHER PUBLICATIONS

U.S. patent application Ser. No. 09/384,717, filed Aug. 26, 1999.
Albarella et al., Nucleic Acids Res. (1989) 17(1):4293.
Chairs et al., J. Med. Chem. (1977) 40:261–266.
Chairs et al., Biochemistry (1996) 35:2047–2053.
Haq et al., J. Mol. Biol. (1997) 271:244–257.
Miller et al., Bioconjug. Chem. (1992) 3(1):74.
Rabin et al., Human Gen. (1987) 75:120.

* cited by examiner

*Primary Examiner*—Gary Benzion
*Assistant Examiner*—Shar Hashemi
(74) *Attorney, Agent, or Firm*—Morrison & Foerster LLP

(57) ABSTRACT

The present invention relates to methods and compositions for analyzing nucleic acids. In particular, the invention provides for methods and combinations for analyzing nucleic acids in a plurality of samples using a plurality of detectably different signature labels and a probe that is hybridizable to each of the target nucleic acids. The invention also provides for a method for quantifying a nucleic acid by analyzing the amount of a label, e.g., a photoactivatable label, attached to the target nucleic acid.

41 Claims, No Drawings

SEQUENCE LISTING

```
<160> NUMBER OF SEQ ID NOS: 2

<210> SEQ ID NO 1
<211> LENGTH: 4
<212> TYPE: PRT
<213> ORGANISM: Artificial Sequence
<220> FEATURE:
<223> OTHER INFORMATION: Angelicin derivative
```

```
-continued

<400> SEQUENCE: 1

Gly Gly Gly Gly
 1

<210> SEQ ID NO 2
<211> LENGTH: 6
<212> TYPE: PRT
<213> ORGANISM: Artificial Sequence
<220> FEATURE:
<223> OTHER INFORMATION: Angelicin derivative

<400> SEQUENCE: 2

Gly Gly Gly Gly Gly Gly
 1               5
```

METHODS AND COMPOSITIONS FOR ANALYZING NUCLEIC ACIDS

FIELD OF THE INVENTION

The present invention relates to methods and compositions for analyzing nucleic acids. In particular, the invention provides for methods and combinations for analyzing nucleic acids in a plurality of samples using a plurality of detectably different signature labels and a probe that is hybridizable to each of the target nucleic acids. The invention also provides for methods for quantifying a nucleic acid by analyzing the amount of a photoactivatable label attached to the target nucleic acid.

BACKGROUND OF THE INVENTION

During the last decade there has been a revolution in the development of microarray technologies. By using a microarray chip, it is possible to get a genetic pattern, including gene expression profile and other information, which were unthinkable in the past. Unfortunately skilled personnel must carry out these methods and very expensive devices must be used to analyze such chips. One major deficiency of the array procedure and most other nucleic acid assay procedures used in a laboratory for identification of a target gene for diagnosis of diseases resides in the inability to analyze multiple samples or target genes by conducting a single hybridization with a probe or a probe cocktail without physically separating either the probes or the samples. This deficiency especially handicaps the utility of nucleic acid hybridization and array technology in high throughput assays by making the large number of assays more costly to perform. The currently available nucleic acid hybridization technologies use one sample one-hybridization format wherein only one sample can be used for hybridization with one probe or one array of nucleic acids immobilized on solid supports.

Accordingly, there is a need in the art for methods and compositions for analyzing nucleic acids wherein target nucleic acids in a plurality of samples can be analyzed concurrently or simultaneously in a single reaction step using a single probe or a cocktail of probes. The present invention addresses this and other related needs in the art.

BRIEF DESCRIPTION OF THE INVENTION

The present invention simplifies nucleic acid hybridization assays and eliminates the need of using complex array system for multi-sample and gene analysis and provides methods for a simplified hybridization analysis in a high throughput assay. The present invention uses, inter alia, signature compounds to label each sample. The labeled samples are then hybridized in a single reaction or container with a probe or a probe cocktail. After the hybridization step, analysis of the signature label in the hybrid duplex establishes the presence, absence and/or amount of the target nucleic acids and identifies which sample(s) contains the target nucleic acid(s).

In one aspect, the present invention is directed to a method for analyzing nucleic acids in a plurality of samples, which method comprises: a) attaching each of target nucleic acids, if there is one in a sample, in a plurality of samples with a signature label, preferably separately, whereby said target nucleic acid in each of said plurality of samples is attached to a detectably different signature label; b) pooling said labeled target nucleic acids in different samples into a single mixture; c) hybridizing each of said labeled target nucleic acids in said single mixture with a probe that is hybridizable to each of said labeled target nucleic acids in a single reaction to form a plurality of target nucleic acid/probe duplexes; and d) determining presence or absence, amount and/or identity of said target nucleic acid in each of said plurality of samples by analyzing presence or absence, amount and/or identity of said signature label in each of said target nucleic acid/probe duplexes.

In another aspect, the present invention is directed to a combination for analyzing nucleic acids in a plurality of samples, which combination comprises a plurality of detectably different signature labels, wherein each of said signature labels is capable of being attached to a target nucleic acid to be analyzed.

In still another aspect, the present invention is directed to a method for quantifying a nucleic acid, which method comprises attaching a label, and preferably a photoactivatable label, to a target nucleic acid and determining amount of said target nucleic acid by analyzing amount of said label attached to said target nucleic acid.

DETAILED DESCRIPTION OF THE INVENTION

A. Definitions

Unless defined otherwise, all technical and scientific terms used herein have the same meaning as is commonly understood by one of ordinary skill in the art to which this invention belongs. All patents, applications, published applications and other publications and sequences from GenBank and other databases referred to herein are incorporated by reference in their entirety. If a definition set forth in this section is contrary to or otherwise inconsistent with a definition set forth in applications, published applications and other publications and sequences from GenBank and other data bases that are herein incorporated by reference, the definition set forth in this section prevails over the definition that is incorporated herein by reference.

As used herein, "a" or "an" means "at least one" or "one or more."

As used herein, "nucleic acid (s)" refers to deoxyribonucleic acid (DNA) and/or ribonucleic acid (RNA) in any form, including inter alia, single-stranded, duplex, triplex, linear and circular forms. It also includes polynucleotides, oligonucleotides, chimeras of nucleic acids and analogues thereof. The nucleic acids described herein can be composed of the well-known deoxyribonucleotides and ribonucleotides composed of the bases adenosine, cytosine, guanine, thymidine, and uridine, or may be composed of analogues or derivatives of these bases. Additionally, various other oligonucleotide derivatives with nonconventional phosphodiester backbones are also included herein, such as phosphotriester, polynucleopeptides (PNA), methylphosphonate, phosphorothioate, polynucleotides primers and the like.

As used herein, "label" refers to any chemical group or moiety having a detectable physical property or any compound capable of causing a chemical group or moiety to exhibit a detectable physical property, such as an enzyme that catalyzes conversion of a substrate into a detectable product. The term "label" also encompasses compound that inhibit the expression of a particular physical property. The "label" may also be a compound that is a member of a binding pair, the other member of which bears a detectable physical property. Exemplary labels include mass groups, metals, fluorescent groups, luminescent groups, chemiluminescent groups, optical groups, charge groups, polar groups, colors, haptens, protein binding ligands, nucleotide sequences, radioactive groups, enzymes, particulate particles and a combination thereof.

As used herein, "detectably different signature label" means that the signature labels can be detected and distinguished from each other by any detection methods and/or instrumentation known in the art. Preferably, the signature labels can be detected and distinguished from each other in an environment suitable for nucleic acid hybridization. Also preferably, the signature labels can be quantified by any detection methods and/or instrumentation known in the art.

As used herein, "pooling said labeled target nucleic acids in different samples into a single mixture" means that target nucleic acid in each of a plurality of samples is mixed together in a single mixture, e.g., solution or fluid. The "pooling" step is conducted concurrently with or subsequent to the "labeling" step wherein the target nucleic acid in each of said plurality of samples is attached to a detectably different signature label. Preferably, "pooling" step is conducted subsequent to the "labeling" step. Although it is preferable that the target nucleic acids from all the samples to be analyzed can be "pooled" together into one single mixture before the hybridizing step, such "complete pooling" is not necessary. It is sufficient that the target nucleic acids from some samples are "pooled together." For example, if target nucleic acids from 100 samples are to be analyzed, the target nucleic acids from some samples, e.g., 10, 20, 30, 40, 50, 60, 70, 80, 90 or all 100 samples, can be pooled for the hybridization analysis.

As used herein, "a probe that is hybridizable to each of the target nucleic acids" refers to a nucleotide sequence that is of suitable length and is sufficiently complementary to a nucleotide sequence in the target nucleic acids that is likely to be present in the samples so that the probe can be hybridized to the target nucleic acids under a suitable condition, e.g., low, middle and high stringency. Preferably, the probe is at least 8, 10, 20, 30, 40, 50 or more than 50 nucleotides long. The probe can be a specific or degenerate probe. Preferably, the probe is specific to the target nucleotide sequence, i.e., is completely complementary to the target nucleotide sequence in the target nucleic acids.

As used herein, "determining presence or absence, amount and/or identity of said target nucleic acid in each of said plurality of samples by analyzing presence or absence, amount and/or identity of said signature label in each of said target nucleic acid/probe duplexes" means that at least two types of information are obtained. First, detection of the formation of the target nucleic acid/probe duplex(es), which is signified by the presence of a label in the duplex, indicates that at least one of the samples has the target nucleic acid(s). Second, detection and identification of a particular signature label, which is distinguishable from other signature labels, indicates which sample has the target nucleic acid(s). For example, 10 samples are analyzed. Nucleic acid in each of the 10 samples is labeled with a fluorescent group and a unique molecular weight group, e.g., one to ten (—$CH_2$) group(s), corresponding to sample number 1–10. The detection of fluorescence in the nucleic acid duplex indicates that at least one sample contains the target nucleic acid. Further identification of the unique molecular weight group identifies which sample(s) has the target nucleic acid. Such analysis can also be conducted without the use of a fluorescent group. The molecular weight of the signature label in each sample will be different because of the number of $CH_2$ groups in the label. Such differences can be monitored directly by mass spectrometric analysis without using any optically detectable label.

As used herein, "a binding ligand that facilitates attachment of said signature label to a target nucleic acid" refers to substance that increase the binding affinity between the label and the target nucleic acid. Ordinarily, the binding ligand should increase the binding affinity between the label and the target nucleic acid by at least 10%, 50%, 1 fold, 5 fold, 10 fold or more than 10 fold. The binding ligand can also increase the binding affinity between the label and the target nucleic acid by functioning as a linker between the label and the target nucleic acid. For example, binding ligand can be a compound that has an affinity for nucleic acids, such that it forms a reversible complex with nucleic acids, and is capable of being activated upon the application of an appropriate wavelength of light to form a covalent bond with the nucleic acids.

As used herein, "a binding enhancer that has a specific affinity for nucleic acids" refers to a chemical moiety that has a specific affinity for nucleic acids, i.e., having higher binding affinity towards nucleic acid than towards other non-nucleic acid materials likely present in the sample such as proteins, lipids, carbohydrates or other macromolecules or small molecules. The binding enhancer can have higher binding affinity towards nucleic acid than towards other non-nucleic acid materials generally or have higher binding affinity towards some or one specific nucleotide sequence(s).

As used herein, "amplification" refers to a method for exponentially duplicating a target analyte nucleic acid in a sample to improve assay sensitivity. As described herein, many different methods for amplifying nucleic acids are known in the art. It should be understood that the particular amplification method employed in the practice of the present invention can vary depending on the type of target analyte, the type of sample, the desired sensitivity, and the like. The selection and performance of such amplification methods are not within the scope of the present invention.

As used herein, "macromolecule" refers to a molecule that, without attaching to another molecule, is capable of generating an antibody that specifically binds to the macromolecule.

As used herein, "small molecule" refers to a molecule that, without forming homo-aggregates or without attaching to a macromolecule or adjuvant, is incapable of generating an antibody that specifically binds to the small molecule. Preferably, the small molecule has a molecular weight that is about or less than 10,000 daltons. More preferably, the small molecule has a molecular weight that is about or less than 5,000 dalton.

As used herein, "vitamin" refers to a trace organic substance required in certain biological species. Most vitamins function as components of certain coenzymes.

As used herein, "lipid" refers to water-insoluble, oily or greasy organic substances that are extractable from cells and tissues by nonpolar solvents, such as chloroform or ether.

As used herein, a "receptor" refers to a molecule that has an affinity for a given ligand. Receptors may be naturally-occurring or synthetic molecules. Receptors may also be referred to in the art as anti-ligands. As used herein, the receptor and anti-ligand are interchangeable. Receptors can be used in their unaltered state or as aggregates with other species. Receptors may be attached, covalently or noncovalently, or in physical contact with, to a binding member, either directly or indirectly via a specific binding substance or linker. Examples of receptors, include, but are not limited to: antibodies, cell membrane receptors surface receptors and internalizing receptors, monoclonal antibodies and antisera reactive with specific antigenic determinants such as on viruses, cells, or other materials, drugs, polynucleotides, nucleic acids, peptides, cofactors, lectins, sugars, polysaccharides, cells, cellular membranes, and organelles.

As used herein, "antibody" includes antibody fragments, such as Fab fragments, which are composed of a light chain and the variable region of a heavy chain. Antibody encompasses polyclonal and monoclonal antibody.

As used herein, "nutrient or storage protein" refers to a protein that is used by the cell as the nutrient source or storage form for such nutrient. Non-limiting examples of nutrient or storage proteins include gliadin, ovalbumin, casein, and ferritin.

As used herein, "contractile or motile protein" refers to a protein that endows cells and organisms with the ability to contract, to change shape, or to move about. Non-limiting examples of contractile or motile proteins include actin, myosin, tubulin and dynein.

As used herein, "structural protein" refers to a protein that serves as supporting filaments, cables, or sheets to give biological structures strength or protection. Non-limiting examples of structural proteins include keratin, fibroin, collagen, elastin and proteoglycans.

As used herein, "defense protein" refers to a protein that defends organisms against invasion by other species or protect them from injury. Non-limiting examples of defense proteins include antibodies, fibrinogen, thrombin, botulinus toxin, diphtheria toxin, snake venoms and ricin.

As used herein, "regulatory protein" refers to a protein that helps regulate cellular or physiological activity. Non-limiting examples of regulatory proteins include insulin, growth hormones, corticotropin and repressors.

As used herein, "sample" refers to anything which may contain an target nucleotide acid to be analyzed. The sample may be a biological sample, such as a biological fluid or a biological tissue. Examples of biological fluids include urine, blood, plasma, serum, saliva, semen, stool, sputum, cerebral spinal fluid, tears, mucus, amniotic fluid or the like. Biological tissues are aggregates of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s). The sample may also be a mixture of target nucleotide acid(s) prepared in vitro.

As used herein, a "liquid sample" refers to a sample that naturally exists as a liquid or fluid, e.g., a biological fluid. A "liquid sample" also refers to a sample that naturally exists in a non-liquid status, e.g., solid or gas, but is prepared as a liquid, fluid, solution or suspension containing the solid or gas sample material. For example, a liquid sample can encompass a liquid, fluid, solution or suspension containing a biological tissue.

As used herein, "expressed in a tissue or organ specific manner" refers to a gene expression pattern in which a gene is expressed, either transiently or constitutively, only in certain tissues or organs, but not in other tissues or organs.

As used herein, "tissue" refers to a collection of similar cells and the intracellular substances surrounding them. There are four basic tissues in the body: 1) epithelium; 2) connective tissues, including blood, bone, and cartilage; 3) muscle tissue; and 4) nerve tissue.

As used herein, "organ" refers to any part of the body exercising a specific function, as of respiration, secretion or digestion.

As used herein, "plant" refers to any of various photosynthetic, eucaryotic multi-cellular organisms of the kingdom Plantae, characteristically producing embryos, containing chloroplasts, having cellulose cell walls and lacking locomotion.

As used herein, "animal" refers to a multi-cellular organism of the kingdom of Animalia, characterized by a capacity for locomotion, nonphotosynthetic metabolism, pronounced response to stimuli, restricted growth and fixed bodily structure. Non-limiting examples of animals include birds such as chickens, vertebrates such fish and mammals such as mice, rats, rabbits, cats, dogs, pigs, cows, ox, sheep, goats, horses, monkeys and other non-human primates.

As used herein, "bacteria" refers to small prokaryotic organisms (linear dimensions of around 1 $\mu$m) with non-compartmentalized circular DNA and ribosomes of about 70 S. Bacteria protein synthesis differs from that of eukaryotes. Many anti-bacterial antibiotics interfere with bacteria proteins synthesis but do not affect the infected host.

As used herein, "eubacteria" refers to a major subdivision of the bacteria except the archaebacteria. Most Gram-positive bacteria, cyanobacteria, mycoplasmas, enterobacteria, pseudomonas and chloroplasts are eubacteria. The cytoplasmic membrane of eubacteria contains ester-linked lipids; there is peptidoglycan in the cell wall (if present); and no introns have been discovered in eubacteria.

As used herein, "archaebacteria" refers to a major subdivision of the bacteria except the eubacteria. There are three main orders of archaebacteria: extreme halophiles, methanogens and sulphur-dependent extreme thermophiles. Archaebacteria differs from eubacteria in ribosomal structure, the possession (in some case) of introns, and other features including membrane composition.

As used herein, "virus" refers to an obligate intracellular parasite of living but non-cellular nature, consisting of DNA or RNA and a protein coat. Viruses range in diameter from about 20 to about 300 nm. Class I viruses (Baltimore classification) have a double-stranded DNA as their genome; Class II viruses have a single-stranded DNA as their genome; Class III viruses have a double-stranded RNA as their genome; Class IV viruses have a positive single-stranded RNA as their genome, the genome itself acting as mRNA; Class V viruses have a negative single-stranded RNA as their genome used as a template for mRNA synthesis; and Class VI viruses have a positive single-stranded RNA genome but with a DNA intermediate not only in replication but also in mRNA synthesis. The majority of viruses are recognized by the diseases they cause in plants, animals and prokaryotes. Viruses of prokaryotes are known as bacteriophages.

As used herein, "fungus" refers to a division of eucaryotic organisms that grow in irregular masses, without roots, stems, or leaves, and are devoid of chlorophyll or other pigments capable of photosynthesis. Each organism (thallus) is unicellular to filamentous, and possesses branched somatic structures (hyphae) surrounded by cell walls containing glucan or chitin or both, and containing true nuclei.

As used herein, "disease or disorder" refers to a pathological condition in an organism resulting from, e.g., infection or genetic defect, and characterized by identifiable symptoms.

As used herein, "infection" refers to invasion of the body of a multi-cellular organism with organisms that have the potential to cause disease.

As used herein, "infectious organism" refers to an organism that is capable to cause infection of a multi-cellular organism. Most infectious organisms are microorganisms such as viruses, bacteria and fungi.

As used herein, neoplasm (neoplasia) refers to abnormal new growth, and thus means the same as tumor, which may be benign or malignant. Unlike hyperplasia, neoplastic proliferation persists even in the absence of the original stimulus.

As used herein, cancer refers to a general term for diseases caused by any type of malignant tumor.

As used herein, a combination refers to any association between two or among more items, e.g., signature labels.

As used herein, a composition refers to any mixture. It may be a solution, a suspension, liquid, powder, paste, aqueous, non-aqueous or any combination thereof.

As used herein: stringency of hybridization in determining percentage mismatch is as follows: (1) high stringency: 0.1×SSPE, 0.1% SDS, 65° C.; (2) medium stringency: 0.2×SSPE, 0.1% SDS, 50° C.; and (3) low stringency: 1.0×SSPE, 0.1% SDS, 50° C. Equivalent stringencies may be achieved using alternative buffers, salts and temperatures.

For clarity of disclosure, and not by way of limitation, the detailed description of the invention is divided into the subsections that follow.

B. Method for Analyzing Nucleic Acids in a Plurality of Samples

In one aspect, the present invention is directed to a method for analyzing nucleic acids in a plurality of samples, which method comprises: a) attaching each of target nucleic acids, if there is one in a sample, in a plurality of samples with a signature label, and preferably separately, whereby said target nucleic acid in each of said plurality of samples is attached to a detectably different signature label; b) pooling said labeled target nucleic acids in different samples into a single mixture; c) hybridizing each of said labeled target nucleic acids in said single mixture with a probe that is hybridizable to each of said labeled target nucleic acids in a single reaction to form a plurality of target nucleic acid/probe duplexes; and d) determining presence or absence, amount and/or identity of said target nucleic acid in each of said plurality of samples by analyzing presence or absence, amount and/or identity of said signature label in each of said target nucleic acid/probe duplexes.

Any suitable label can be used in the present method. Exemplary labels include a mass group, a metal, a fluorescent group, a luminescent group, a chemiluminescent group, e.g., an acridinium ester, an optical group, a charge group, a polar group, a color, a hapten, an antibody, an epitope-containing compound, a protein binding ligand, a nucleotide sequence, a radioactive group, an enzyme, an enzyme substrate, a particulate particle, a magnetically responsive compound and a combination thereof. The labels can be same kind or different kinds of substances. In a preferred embodiment, the labels used in the method are composites made of a plurality of substances and the labels are different from each other because they contain different kinds of substances having different chemical or physical composition or properties and/or contain same kinds of substances at different ratios.

Any suitable samples can be analyzed by the present method. For example, biological, agricultural, veterinary, environmental, or human samples can be analyzed. Preferably, clinical samples are analyzed. Any suitable target nucleic acids can be analyzed by the present method. Preferably, the target nucleic acids to be analyzed are nucleic acid amplification products. For example, the target nucleic acids can be amplification products of any known nucleic acid amplification methods such as polymerase chain reaction (PCR) (U.S. Pat. Nos. 4,683,195 and 4,683,202), ligase chain reaction (LCR), nucleic acid sequence-based amplification (NASBA) (U.S. Pat. Nos. 5,409,818 and 5,554,517), strand displacement amplification (SDA) and transcription-medicated amplification (TMA).

The labels can be attached to the target nucleic acids by any suitable methods known in the art. For example, the labels can be attached to the target nucleic acids covalently or non-covalently. The labels can also be attached to the target nucleic acids directly or indirectly via a linker. Preferably, the labels are attached to the target nucleic acids via a cleavable linkage or linker, e.g., the linkage or linker that is cleavable via a physical, a chemical or an enzymatic treatment.

The analysis can be conducted on a surface. For example, the probe can be immobilized on a surface and the target nucleic acids and the probe can be hybridized on said surface. Any suitable surface can be used. For example, the surface can be a silicon, e.g., silicon dioxide or silicon nitride, a plastic, a glass, a ceramic, a rubber, a polymer surface and a combination thereof. The surface can be hydrophobic or hydrophilic. The surface can be in any suitable shape such as sphere, square, rectangle, triangle, circular disc, cube-like shape or other regular or irregular shape. The surface can be in any suitable dimension(s). Preferably, the probe is immobilized in a plurality of areas on the surface.

The analysis can be conducted in a fluid or liquid. For example, the target nucleic acids and the probe can be hybridized in a liquid. Preferably, the hybridization is conducted in a liquid container such as a beaker, a flask, a cylinder, a test tube, an eppendorf tube, a centrifugation tube, a culture dish and a multiwell plate.

In solution, immobilizable probe(s) can be hybridized with different samples labeled with signature probes and after hybridization, hybrids are separated and analyzed for the signature compound. Such immobilizable probe can be synthesized with biotinylation and hybrid separation can be carried out using streptavidin coated polystyrene beads. All known hybridization formats, whether it is in solution or on beads or plates or other surfaces, can be used to carry out the present invention. The present invention is not limited to the selection of hybridization method. Any alteration or modification, which may be needed to conduct the multi-analyte assay using the present invention, can be easily accomplished by any one skilled in the art.

The pooling step can be conducted at suitable times relative to other steps in the present method. For example, the pooling step can be conducted prior to or concurrently with the hybridizing step. Preferably, the pooling step is conducted prior to the hybridizing step, i.e., the target nucleic acids are labeled with signature labels before they are pooled together for the hybridization analysis. Alternatively, the pooling step can be conducted after the hybridizing step but prior to or concurrently with the determining step, i.e., the target nucleic acids are labeled with signature labels and hybridized with the probes before they are pooled together for determining presence or absence, amount and/or identity of the signature label in each of the target nucleic acid/probe duplexes.

The signature labels used in the present method can be contained in a composition comprising the signature label and a binding ligand that facilitates attachment of said signature label to a target nucleic acid. Any suitable binding ligand can be used. In one example, the binding ligand can comprise a chemical moiety that binds to a target nucleic acid and that, when activated by light, forms at least one covalent bond with the target nucleic acid. In another example, the binding ligand can be an intercalator such as a furocoumarin, a phenanthridine, a monoadduct forming compound or an angelicin derivative. In still another example, the binding ligand can be a non-intercalator such as a benzimide, a netropsin and a distamycin. Preferably, the binding ligand is a photoreactive binding ligand.

Other suitable binding ligands, including the ones disclosed in U.S. Pat. No. 6,187,566, can be used. For example, the binding ligand used in the present method can preferably be any photoreactive chemical moiety that reversibly binds to nucleic acids and forms at least one covalent bond with the nucleic acid when exposed to light of an appropriate wavelength. In a preferred embodiment, the photoreactive binding ligand is an intercalator compound, i.e., a compound that interposes itself between the nucleotide bases of a nucleic acid helix. Suitable intercalator binding ligands include, inter alia, furocoumarins and phenanthridines. For binding to DNA, aminomethyl psoralen, aminomethyl angelicin and aminoalkyl ethidium or methidium azides are useful. Although these compound preferentially bind to double-stranded DNA, conditions can be employed to denture the DNA to avoid simultaneous interaction of these compound with two stands.

In order to preserve the ability of the labeled amplicon to participate in hybridization reactions, it is desirable to use binding ligands that react with a single nucleic acid strand. Accordingly, preferred binding ligands are "monoadduct" forming compound such as isopsoralen or other angelicin derivatives, such as 4'-aminomethyl 4,5'-dimethyl angelicin, 4'-aminomethyl 4,5', 8-trimethyl psoralen, 3-carboxy-5-or 8-amino-or hydroxy-psoralen, as well as mono-or bis-azido aminoalkyl methidium or ethidium compound. For examples of other photoreactive intercalators, see U.S. Pat. No. 4,734,454.

Nonintercalating compound, such as diamidinoindophenol-bis-benzimidazoles, which are commonly known as Hoechst 33258 and 33342, and other benzimides, netropsins and distamycins can also be used in the present method. Preferred photoreactive binding ligands are the monoadduct forming psoralens and isopsoralens.

The composition used in the present method can further comprise, in addition to the label and binding ligand, a binding enhancer that has a specific affinity for nucleic acids. Any suitable binding enhancer can be used. For example, the binding enhancer is an intercalator, e.g., a monoadduct forming compound, or a non-intercalator, e.g., an oligo pyrrole, a phenyl indole, a nucleic acid and a protein. Preferably, the binding enhancer has an affinity for nucleic acids equal to or greater than $1 \times 10^4$ mole$^{-1}$, specifically binds to nucleic acids in the presence of greater than 10 mM magnesium or comprises a nucleotide sequence that specifically binds to a target nucleic acid to be analyzed.

Other suitable binding enhancers, including the ones disclosed in U.S. Pat. No. 6,187,566, can be used. For example, the binding enhancers can have a specific affinity for nucleic acids when compare to non-nucleic acid sample/reaction constituents. The binding enhancer may be the same as or different from the binding ligand. In other words, the binding ligand and the binding enhancer may each be an intercalator, wherein one of the two is a monoadduct-forming species, and the other is present to enhance binding by this monoadduct-forming species. Examples of such "dual role" binding ligands are described in Chaires et al., *J. Med. Chem.*, 40:261–266 (1977). Therein, it has been described that binding of a bis-intercalating anthracycline antibiotic reached as high as $10^{11}$ mole$^{-1}$ at 20° C. It was also shown that the affinity of a similar monointercalator is not above $10^7$ mole$^{-1}$ (Chaires et al., *Biochemistry*, 35:2047–2053 (1996)).

The binding enhancer can also be a non-intercalating compound. There are many nonintercalating nucleic acid binding molecules known in the art. A bisbenzimidazole derivative commonly known as Hoechst 33258 has shown affinity as high as $3.2 \times 10^8$ mole$^{-1}$. (Haq et al., *J. Mol. Biol.*, 271:244–257 (1997)). Other non-intercalating binding enhancers are oligo pyrroles, phenyl indole derivatives and such molecules. These molecules do not bind nucleic acids only on the basis of positive charge. Other suitable binding enhancers bind nucleic acids on the basis of hydrogen bond formation, hydrophobic interaction in the groove and other nonionic interactions that give rise to high affinity reactions with nucleic acids. In general, preferred binding enhancers will exhibit an affinity for nucleic acids in an amount equal to or greater than $1 \times 10^4$ mole$^{-1}$. Other suitable binding enhancers include nucleic acids having a specific affinity for other nucleic acids, such as would be expected if the binding enhancer had a nucleic acid sequence complementary to that of the amplicon target nucleic acid. Yet other suitable binding enhancers include proteins that have a specific binding affinity for nucleic acids.

Not every compound capable of forming an electrostatic bond with a negatively charged nucleic acid can serve as a binding enhancer. For example, polycations such as polyamines are generally not suitable for use in the present invention because of their inability to specifically bind to nucleic acids in crude samples and in the presence of amplification reaction components. For example, such positively charged compound will nonspecifically bind to all anionic macromolecules present in the sample, and not just to nucleic acids. In addition, the binding enhancer should be capable of specifically binding to nucleic acids in the presence of 10 to 20 mM magnesium, which is typically required for most amplification reactions. At this concentration, compound that bind to nucleic acids solely on the basis of electrostatic interactions would not form stable complexes with nucleic acids and thus would require addition of a greater concentration of the composition for efficient labeling.

In a specific embodiment, both the binding ligand and the binding enhancer are intercalator moieties and wherein at least one of said intercalator moieties forms at least one covalent bond with a nucleic acid to be analyzed.

In another specific embodiment, the binding ligand, binding enhancer and signature label in at least one of the compositions are bound together in the form of a covalent or noncovalent complex. The label can be linked to the binding ligand and/or binding enhancer by any methods known in the art via any suitable linkage. For example, the signature label can be linked to the binding ligand and/or binding enhancer in the complex directly or indirectly via a linker. The signature label can also be linked to the binding ligand and/or binding enhancer in the complex via a cleavable linkage or linker. The linkage or linker can be cleavable via a physical, a chemical or an enzymatic treatment.

The composition comprising a label, a binding ligand and a binding enhancer can be complexed together in any suitable format. For example, the complex can have a linear format: label-binding ligand-binding enhancer; label-binding enhancer-binding ligand; binding ligand-label-binding enhancer; binding ligand-binding enhancer-label; binding enhancer-binding ligand-label; and binding enhancer-label-binding ligand. Alternatively, the complex can have a branch format as given below:

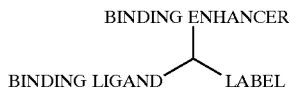

In this example, the binding ligand, binding enhancer and label are all interconnected to one another.

In a specific embodiment, the composition comprising a label, a binding ligand and a binding enhancer can be a "light-activated compound" ("LAC"), such as the one disclosed in U.S. Pat. No. 6,187,566. LAC is particularly useful in analyzing nucleic acid amplification product in the present method because LAC can serve the dual purpose of labeling and "deactivating" the amplicons. By "deactivating", it is meant that the photo-activated amplicons can no longer be amplified. In particular, the LAC is added to the amplification reaction before, during or after the nucleic acid amplification reaction. After the amplification reaction is completed, the reaction mixture is exposed to light of an appropriate wavelength to cause the labeling compound to become covalently linked to the amplicon. Thereafter, the amplicon is incapable of serving as a template for polymerization and thus prevented from contaminating subsequent amplification reactions.

The LACs that are useful in the practice of the present method are designed to be compatible with any target amplification protocol, and can be added to the amplification reaction before, during or after the initiation of the amplification reaction. In particular, the LACs can be designed to have an enhanced affinity for nucleic acids so that they will efficiently bind to nucleic acid in the presence of other sample and amplification reaction constituents, such as proteins, lipids, enzymes, multivalent cations, etc. Such enhanced affinity permits a lower concentration of LAC to be necessary for efficient decontamination and labeling. Thus, a noninhibitory amount of LAC can be added to the amplification reaction mixture before amplification has taken place. Thereafter, the LAC can be exposed to light to effect simultaneous decontamination and labeling.

The present method can further comprise a step of releasing target nucleic acids from a sample source. The target nucleic acids can be released from a sample source by any suitable methods known in the art. In a specific embodiment, the target nucleic acids can be released and labeled concurrently using a composition comprising a signature label and a lysing agent for releasing nucleic acids. In another specific embodiment, the composition comprising a label, a binding ligand and a binding enhancer can further comprise a lysing reagent for releasing a target nucleic acid to be analyzed.

Any suitable lysing reagent for releasing nucleic acids can be used (See e.g., Ausubel et al. (Ed.), *Current Protocols in Molecular Biology* John Wiley & Sons, Inc. (1998)). For example, lysing reagent/compositions disclosed in the co-pending U.S. patent application Ser. No. 09/385,624, filed Aug. 26, 1999 (now U.S. Pat. No. 6,242,624), can be used. In particular, a composition for releasing nucleic acid from a sample in a form suitable for directly detecting the nucleic acid can be used, which composition comprises: an aqueous solution comprising one or more lipids for releasing nucleic acid from the sample and further comprising one or more of: i) an enzyme(s) to degrade cell structure; ii) a non-ionic membrane fluidizing compound(s); and iii) a metal chelator(s); wherein said aqueous solution is non-denaturing and non-inhibitory of enzymes or proteins used in nucleic acid release, amplification, labeling or detection. Another composition for releasing nucleic acid from a sample in a form suitable for directly detecting the nucleic acid can also be used, which composition comprises: an aqueous solution of a non-ionic membrane fluidizing compound(s), and further one or more of: i) an enzyme(s) to degrade cell structure; ii) a lipid(s); and iii) a metal chelator (s); wherein said aqueous solution is non-denaturing and non-inhibitory of enzymes or proteins used in nucleic acid release, amplification, labeling or detection.

In another example, lysing reagent/compositions disclosed in the co-pending U.S. patent application Ser. No. 09/384,717, filed Aug. 26, 1999 (now U.S. Pat. No. 6,379,930), can be used. In particular, a composition comprising a cocktail of reagents for performing nucleic acid amplification that avoids undesirable reactions between the individual reagents, thereby stabilizing the cocktail upon storage, can be used, which composition comprises one or more of the reagents necessary to perform nucleic acid amplification and an inhibitory concentration of a reversible inhibitor(s) of the undesirable reaction.

According to the present method, the presence or absence, amount and/or identity of the target nucleic acid in each of the plurality of samples is determined by the analyzing presence or absence, amount and/or identity of the signature label in each of the target nucleic acid/probe duplexes. The presence or absence, amount and/or identity of the signature label in each of the target nucleic acid/probe duplexes can be determined by any methods known in the art, provided that the label and the detection method/instrumentation are compatible with each other.

For example, if a mass group is used as a label, any method for detecting mass can be used as the detection method. Exemplary methods include mass spectrometry, chromatography, electrophoresis, filtration or centrifugation, etc. Preferably, mass spectrometry is used. Any type of mass spectrometry analysis can be used (See generally *Introduction to Mass Spectrometry*, (3rd Ed.) Watson (Ed)., Lippincott-Raven Publishers (1997)). For example, Fast Atom Bombardment (FAB), Matrix-Assisted Laser Desorption/Ionization (MALDI) including UV-MALDI and IR-MALDI, Electrospray Ionization (EI) mass spectrometry can be used. The mass spectrometry can be used alone or be used in combination with other detection methods such as Gas Chromatography—Mass Spectrometry (GC-MS) and Liquid Chromatography—Mass Spectrometry (LC-MS). In a specific embodiment, mass spectrometry methods disclosed in the following U.S. patent Nos. can be used: U.S. Pat. Nos. 6,139,800, 6,057,107, 6,046,807, 5,981,180, 5,802,327 and 5,736,330.

If other types of label are used, e.g., a metal, a fluorescent group, a luminescent group, a chemiluminescent group, an optical group, a charge group, a polar group, a color, a hapten, an antibody, an epitope-containing compound, a protein binding ligand, a nucleotide sequence, a radioactive group, an enzyme, an enzyme substrate, a particulate particle, e.g., colloidal gold, a magnetically responsive compound and a combination thereof, corresponding compatible detection methods/instrumentation should be used (See e.g., Thomsen, *Modern Spectrochemical Analysis of Metals: An Introduction for Users of ARC/Spark Instrumentation,* A S M International (1996); Lobinski and Marczenko, *Spectrochemical Trace Analysis for Metals and Metalloids,* Elsevier Science (1997); Mason and Mason, *Fluorescent and Luminescent Probes: A Practical Guide to Technology for Quantitative Real-Time Analysis Revised,* Academic Press, Incorporated (1999); Jameson and Reinhart, *Fluorescent Biomolecules: Methodologies and Applications,* Perseus Books (1989); U.S. Pat. No. 5,850,479 entitled "Optical feature extraction apparatus and encoding method for detection of DNA sequences;" U.S. Pat. No. 5,498,279 entitled "High speed gas chromatography system for analysis of polar organic compounds;" U.S. Pat. No. 4,838,697 entitled "Apparatus for rapid colorimetry on different samples;" Coligan et al. (Ed.), *Current Protocols in Immunology*, John Wiley & Sons, Inc. (2000); U.S. Pat. No. 6,148,658 entitled "System and method for isotope ratio analysis and gas detection by photoacoustics;" Hayat (Ed.), *Colloidal Gold: Principles, Methods and Applications*, Vol. 2, Academic Press, Incorporated (1989); and Ausubel et al. (Ed.), *Current Protocols in Molecular Biology* John Wiley & Sons, Inc. (1998).

The present method can also be used to analyze target nucleic acids with a plurality of probes so that each of the probes hybridizes to a different kind of target nucleic acid. It is possible to hybridize different samples labeled differently to multiple probes. For example, sample 1 suspected of containing homozygous sickle hemoglobin gene can be labeled with probe ix, sample 2 suspected of containing homozygous normal hemoglobin gene can be labeled with probe iix and sample 3 suspected of containing heterozygous can be labeled with probe iiix. All these samples can be hybridized together to a probe cocktail containing sickle and normal hemoglobin probes. In the hybrid, the presence of the particular label can be used to determine the globulin gene type in the samples. Preferably, the labeled target nucleic acids are hybridized to the plurality of probes simultaneously.

C. Combination for Analyzing Nucleic Acids in a Plurality of Samples

In another aspect, the present invention is directed to a combination for analyzing nucleic acids in a plurality of samples, which combination comprises a plurality of detectably different signature labels, wherein each of said signature labels is capable of being attached to a target nucleic acid to be analyzed.

Any suitable label can be used in the present combination. Exemplary labels include a mass group, a metal, a fluorescent group, a luminescent group, a chemiluminescent group, an optical group, a charge group, a polar group, a color, a hapten, an antibody, an epitope-containing compound, a protein binding ligand, a nucleotide sequence, a radioactive group, an enzyme, an enzyme substrate, a particulate particle, a magnetically responsive compound and a combination thereof. The labels can be same kind or different kinds of substances. In a preferred embodiment, the labels used in the combination are composites made of a plurality of substances and the labels are different from each other because they contain different kinds of substances having different chemical or physical composition or properties and/or contain same kinds of substances at different ratios.

The signature labels used in the present combination can be contained in a composition comprising the signature label and a binding ligand that facilitates attachment of said signature label to a target nucleic acid. Any suitable binding ligand can be used. In one example, the binding ligand can comprise a chemical moiety that binds to a target nucleic acid and that, when activated by light, forms at least one covalent bond with the target nucleic acid. In another example, the binding ligand can be an intercalator such as a furocoumarin, a phenanthridine, a monoadduct forming compound or an angelicin derivative. In still another example, the binding ligand can be a non-intercalator such as a benzimide, a netropsin and a distamycin. Preferably, the binding ligand is a photoreactive binding ligand. Other suitable binding ligands, including the ones disclosed in U.S. Pat. No. 6,187,566, can be used.

The composition used in the present combination can further comprise, in addition to the label and binding ligand, a binding enhancer that has a specific affinity for nucleic acids. Any suitable binding enhancer can be used. For example, the binding enhancer is an intercalator, e.g., a monoadduct forming compound, or a non-intercalator, e.g., an oligo pyrrole, a phenyl indole, a nucleic acid and a protein. Preferably, the binding enhancer has an affinity for nucleic acids equal to or greater than $1 \times 10^4$ mole$^{-1}$, specifically binds to nucleic acids in the presence of greater than 10 mM magnesium or comprises a nucleotide sequence that specifically binds to a target nucleic acid to be analyzed. Other suitable binding enhancers, including the ones disclosed in U.S. Pat. No. 6,187,566, can be used.

In a specific embodiment, both the binding ligand and the binding enhancer are intercalator moieties and wherein at least one of said intercalator moieties forms at least one covalent bond with a nucleic acid to be analyzed.

In another specific embodiment, the binding ligand, binding enhancer and signature label in at least one of the compositions are bound together in the form of a covalent or noncovalent complex. The label can be linked to the binding ligand and/or binding enhancer by any methods known in the art via any suitable linkage. For example, the signature label can be linked to the binding ligand and/or binding enhancer in the complex directly or indirectly via a linker. The signature label can also be linked to the binding ligand and/or binding enhancer in the complex via a cleavable linkage or linker. The linkage or linker can be cleavable via a physical, a chemical or an enzymatic treatment.

The composition comprising a label, a binding ligand and a binding enhancer can be complexed together in any suitable format. For example, the complex can have a linear format: label-binding ligand-binding enhancer; label-binding enhancer-binding ligand; binding ligand-label-binding enhancer; binding ligand-binding enhancer-label; binding enhancer-binding ligand-label; and binding enhancer-label-binding ligand. Alternatively, the complex can have a branch format as given below:

In this example, the binding ligand, binding enhancer and label are all interconnected to one another.

In a specific embodiment, the composition comprising a label, a binding ligand and a binding enhancer can be a "light-activated compound" ("LAC"), such as the one disclosed in U.S. Pat. No. 6,187,566. LAC is particularly useful in analyzing nucleic acid amplification product in the present method because LAC can serve the dual purpose of labeling and "deactivating" the amplicons.

The combination/composition comprising a label can further comprise any or all of a binding ligand, a binding enhancer and a lysing reagent for releasing a target nucleic acid to be analyzed. Any suitable lysing reagent for releasing nucleic acids can be used. For example, lysing reagent/compositions disclosed in the co-pending U.S. patent application Ser. Nos. 09/385,624 and 09/384,717, both filed Aug. 26, 1999, can be used.

D. Methods for Quantifying Nucleic Acids

In still another aspect, the present invention is directed to a method for quantifying a nucleic acid, which method comprises attaching a label, preferably a photoactivatable label, to a target nucleic acid and determining amount of said target nucleic acid by analyzing amount of said label attached to said target nucleic acid.

Any suitable label can be used in the present method. Exemplary labels include a mass group, a metal, a fluorescent group, a luminescent group, a chemiluminescent group, an optical group, a charge group, a polar group, a color, a hapten, an antibody, an epitope-containing compound, a protein binding ligand, a nucleotide sequence, a radioactive group, an enzyme, an enzyme substrate, a particulate particle, magnetically responsive compound and a combination thereof. The labels can be same kind or different kinds of substances. In a preferred embodiment, the labels used in the method are composites made of a plurality of substances and the labels are different from each other because they contain different kinds of substances having different chemical or physical composition or properties and/or contain same kinds of substances at different ratios.

Any suitable samples can be analyzed by the present method. For example, biological, agricultural, veterinary, environmental, or human samples can be analyzed. Preferably, clinical samples are analyzed. Any suitable target nucleic acids can be quantified by the present method. Preferably, the target nucleic acids to be quantified are nucleic acid amplification products.

The labels can be attached to the target nucleic acids by any suitable methods known in the art. For example, the labels can be attached to the target nucleic acids covalently or non-covalently. The labels can also be attached to the target nucleic acids directly or indirectly via a linker. Preferably, the labels are attached to the target nucleic acids via a cleavable linkage or linker, e.g., the linkage or linker that is cleavable via a physical, a chemical or an enzymatic treatment.

The analysis can be conducted on a surface. Any suitable surface can be used. For example, the surface can be a silicon, e.g., silicon dioxide or silicon nitride, a plastic, a glass, a ceramic, a rubber, a polymer surface and a combination thereof. The surface can be hydrophobic or hydrophilic. The surface can be in any suitable shape such as sphere, square, rectangle, triangle, circular disc, cube-like shape or other regular or irregular shape. The surface can be in any suitable dimension(s). If the method further comprises a step of hybridizing the target nucleic acid to a probe, the probe can be immobilized on the surface, and preferably immobilized in a plurality of areas on the surface. The analysis can also be conducted in a fluid or liquid, e.g., conducted in a liquid container such as a beaker, a flask, a cylinder, a test tube, an eppendorf tube, a centrifugation tube, a culture dish and a multiwell plate.

The label used in the method can be used alone. Alternatively, the label can be contained in a composition comprising said label and a binding ligand that facilitates attachment of said label to a target nucleic acid. Any suitable binding ligand can be used. In one example, the binding ligand can comprise a chemical moiety that binds to a target nucleic acid and that, when activated by light, forms at least one covalent bond with the target nucleic acid. In another example, the binding ligand can be an intercalator such as a furocoumarin, a phenanthridine, a monoadduct forming compound or an angelicin derivative. In still another example, the binding ligand can be a non-intercalator such as a benzimide, a netropsin and a distamycin. Preferably, the binding ligand is a photoreactive binding ligand. Other suitable binding ligands, including the ones disclosed in U.S. Pat. No. 6,187,566, can be used.

The composition used in the present method can further comprise, in addition to the label and binding ligand, a binding enhancer that has a specific affinity for nucleic acids. Any suitable binding enhancer can be used. For example, the binding enhancer is an intercalator, e.g., a monoadduct forming compound, or a non-intercalator, e.g., an oligo pyrrole, a phenyl indole, a nucleic acid and a protein. Preferably, the binding enhancer has an affinity for nucleic acids equal to or greater than $1 \times 10^4$ mole$^{-1}$, specifically binds to nucleic acids in the presence of greater than 10 mM magnesium or comprises a nucleotide sequence that specifically binds to a target nucleic acid to be analyzed. Other suitable binding enhancers, including the ones disclosed in U.S. Pat. No. 6,187,566, can be used.

In a specific embodiment, both the binding ligand and the binding enhancer are intercalator moieties and wherein at least one of said intercalator moieties forms at least one covalent bond with a nucleic acid to be analyzed.

In another specific embodiment, the binding ligand, binding enhancer and signature label in at least one of the compositions are bound together in the form of a covalent or noncovalent complex. The label can be linked to the binding ligand and/or binding enhancer by any methods known in the art via any suitable linkage. For example, the signature label can be linked to the binding ligand and/or binding enhancer in the complex directly or indirectly via a linker. The signature label can also be linked to the binding ligand and/or binding enhancer in the complex via a cleavable linkage or linker. The linkage or linker can be cleavable via a physical, a chemical or an enzymatic treatment.

The composition comprising a label, a binding ligand and a binding enhancer can be complexed together in any suitable format. For example, the complex can have a linear format: label-binding ligand-binding enhancer; label-binding enhancer-binding ligand; binding ligand-label-binding enhancer; binding ligand-binding enhancer-label; binding enhancer-binding ligand-label; and binding enhancer-label-binding ligand. Alternatively, the complex can have a branch format as given below:

In this example, the binding ligand, binding enhancer and label are all interconnected to one another.

In specific embodiment, the composition comprising a label, a binding ligand and a binding enhancer can be a "light-activated compound" ("LAC"), such as the one disclosed in U.S. Pat. No. 6,187,566. LAC is particularly useful in analyzing nucleic acid amplification product in the present method because LAC can serve the dual purpose of labeling and "deactivating" the amplicons.

The present method can further comprise a step of releasing target nucleic acids from a sample source. The target nucleic acids can be released from a sample source by any suitable methods known in the art. In a specific embodiment, the target nucleic acids can be released and labeled concurrently using a composition comprising a signature label and a lysing agent for releasing nucleic acids. In another specific embodiment, the composition comprising a label, a binding ligand and a binding enhancer can further comprise a lysing reagent for releasing a target nucleic acid to be analyzed. Any suitable lysing reagent for releasing nucleic acids can be used. For example, lysing reagent/compositions disclosed in the co-pending U.S. patent application Ser. Nos. 09/385,624 and 09/384,717, both filed Aug. 26, 1999, can be used.

E. Test Samples and Target Nucleotide Sequences

Target nucleotide sequences that can be analyzed and/or quantified using the present methods and/or combinations disclosed herein in Sections B, C and D can be DNA, RNA or any other naturally or synthetic nucleic acid sample. Test samples can include body fluids, such as urine, blood, semen, cerebrospinal fluid, pus, amniotic fluid, tears, or semisolid or fluid discharge, e.g., sputum, saliva, lung aspirate, vaginal or urethral discharge, stool or solid tissue samples, such as a biopsy or chorionic villi specimens. Test samples also include samples collected with swabs from the skin, genitalia, or throat. Test samples can be processed to isolate nucleic acid by a variety of means well known in the art.

Although the present methods and/or combinations can be used in solution, it can also be conducted in chip format, e.g., by using the probe(s) immobilized on a solid support.

Similarly, although the present methods and/or combinations can be used to analyze a single sample with a single probe at a time. Preferably, the method is conducted in high-throughput format. For example, a plurality of samples can be analyzed with a single probe simultaneously, or a single sample can be analyzed using a plurality of probes simultaneously. More preferably, a plurality of samples can be analyzed using a plurality of probes simultaneously.

Any suitable target nucleic acids can be analyzed using the present method and/or combinations. Exemplary target nucleic acids include DNA, such as A-, B- or Z-form DNA, and RNA such as mRNA, tRNA and rRNA. The nucleic acids can be single-, double- and triple-stranded nucleic acids. In addition, target nucleic acids encoding proteins and/or peptides can be analyzed. Exemplary proteins or peptides include enzymes, transport proteins such as ion channels and pumps, nutrient or storage proteins, contractile or motile proteins such as actins and myosins, structural proteins, defense proteins or regulatory proteins such as antibodies, hormones and growth factors.

Any suitable samples can be analyzed using the present method and/or combinations. Preferably, a biosample is analyzed using the present method. For example, a biosample of plant, animal, human, fungus, bacterium and virus origin can analyzed. If a sample of a mammal or human origin is analyzed, the sample can be derived from a particular tissue or organ. Exemplary tissues include connective, epithelium, muscle or nerve tissue. Exemplary organs include eye, annulospiral organ, auditory organ, Chievitz organ, circumventricular organ, Corti organ, critical organ, enamel organ, end organ, external female gential organ, external male genital organ, floating organ, flower-spray organ of Ruffini, genital organ, Golgi tendon organ, gustatory organ, organ of hearing, internal female genital organ, internal male genital organ, intromittent organ, Jacobson organ, neurohemal organ, neurotendinous organ, olfactory organ, otolithic organ, ptotic organ, organ of Rosenmüller, sense organ, organ of smell, spiral organ, subcommissural organ, subfornical organ, supernumerary organ, tactile organ, target organ, organ of taste, organ of touch, urinary organ, vascular organ of lamina terminalis, vestibular organ, vestibulocochlear organ, vestigial organ, organ of vision, visual organ, vomeronasal organ, wandering organ, Weber organ and organ of Zuckerkandl. Preferably, samples derived from an internal mammalian organ such as brain, lung, liver, spleen, bone marrow, thymus, heart, lymph, blood, bone, cartilage, pancreas, kidney, gall bladder, stomach, intestine, testis, ovary, uterus, rectum, nervous system, gland, internal blood vessels, etc, are analyzed.

Alternatively, pathological samples in connection with various diseases or disorders or infections can be analyzed. Exemplary diseases or disorders include neoplasms (neoplasia), cancers, immune system diseases or disorders, metabolism diseases or disorder, muscle and bone diseases or disorders, nervous system diseases or disorders, signal diseases or disorders and transporter diseases or disorders. The infection to be analyzed can be fungal, bacterial and viral infection.

The present methods can be used to detect or analyze any nucleic acids from essentially any species of organism, including, for example, Acintobacter, Actinomyces, Aerococcus, Aeromonas, Alclaigenes, Bacillus, Bacteriodes, Bordetella, Branhamella, Bevibacterium, Campylobacter, Candida, Capnocytophagia, Chlamydia, Chromobacterium, Clostridium, Corynebacterium, Cryptococcus, Deinococcus, Enterococcus, Erysielothrix, Escherichia, Flavobacterium, Gemella, Gonorrhea, Haemophilus, Klebsiella, Lactobacillus, Lactococcus, Legionella, Leuconostoc, Listeria, Micrococcus, Mycobacterium, Neisseria, Nocardia, Oerskovia, Paracoccus, Pediococcus, Peptostreptococcus, Propionibacterium, Proteus, Psuedomonas, Rahnella, Rhodococcus, Rhodospirillium, Staphlococcus, Streptomyces, Streptococcus, Vibrio, and Yersinia. Also included are viruses such as the hepatitis viruses and human immunodeficiency viruses (HIV).

F. Examples

The present invention is useful in analyzing more than one target by hybridization to a single probe immobilized as a single point. Such analysis is also possible in solution. Multiple analytes can be analyzed by mass spectrometric, chromatographic or capillary electrophoresis detection of nucleic acid hybrids following photochemical labeling of the target nucleic acids.

For example, a series of samples from different patients suspected of having tuberculosis are collected in different sample collection tubes. Each tube is processed to release nucleic acids and to each tube a separate compound capable of reacting with sample nucleic acids is added. The reaction is carried out and the resulting mixtures containing labeled nucleic acids are hybridized to a mycobacterium tuberculosis specific probe immobilized onto magnetic micro particles. The single particle suspension is used to hybridize with all the samples. After hybridization and washing steps, the labels are detected by mass spectrometry, e.g., MALDI. Since every labeling compound has a different mass and a specific compound has been used to label a specific sample, presence of the compound in the hybrid will determine the presence of the target sequence in the patient's sample. Such multiple sample analysis can also be carried out with other types of compounds, which have distinct fluorescence, luminescence or other electronic properties.

Exemplary label can be a series of mass groups such as Angelicin, Angelicin-R, Angelicin-RR, Angelicin-RRR, Angelicin-RRRR and Angelicin-RRRRR, etc, wherein R stands for alkyl residues. Alkyl residues in different compounds can be identical or different or a mixture of compounds. These moieties will provide differentiation in the signature of the compounds for identification.

Such label compounds can be synthesized by reacting amino methyl angelicin with alkyl halides. Similar compounds with different linkage can also be made by reacting amino compounds with activated carboxyl compounds. Besides alkyl or aryl or other purely organic signature generating moieties, the present invention can also utilize compounds of bioorganic in nature. For example, a nucleic acid modifying compound can be derivatized with peptide of different lengths to create molecules of distinct signature: Angelicin-gly, Angelicin-gly-gly, Angelicin-gly-gly-gly, Angelicin-gly-gly-gly-gly (SEQ ID NO:1), Angelicin-gly-gly-gly-gly-gly, etc (SEQ ID NO:2). Such molecules can be synthesized in a commercially available solid phase peptide synthesizer.

By following the methods described above the signature compounds can be made to carry defined mass, charge or other optical and luminescent properties. By using compounds capable of binding metals, specific signature compounds can be made by reacting with metals of different atomic weights. For example, EDTA is initially coupled to angelicin and then it is photo-chemically coupled to target nucleic acid samples. After this step, water soluble salts of metal ions like iron, platinum, palladium etc. are added to different sample, excess metal ions are removed before the labeled samples are used.

Specific signature modification can also be done without using the nucleic acid binding ligands. For example, target nucleic acid can be chemically modified via a transamination reaction to modify cytosine residues, which can then be reacted with activated signature generating compounds.

The label compounds can be detected directly or after photo reversal. The compounds can be linked through linkers, which are also hydrolysable under mild chemical conditions prior to detection. The compounds can be made to have positive or negative charges or neutral in ionic character.

The samples to be analyzed can be amplicons of different amplification reactions. In a screening or clinical laboratory, patient blood samples can be amplified as individual sample. Specific signature compounds are added to different amplicons and photoreaction is conducted. All samples are then hybridized to an immobilized probe in a single reaction. After hybridization, presence of different compounds is analyzed to determine which sample contained the suspected organism.

EXAMPLE 1

Synthesis of Signature Compounds for Mass Spectrometric Analysis

4'-aminomethyl-4,5'-dimethyl angelicin (AMA) is prepared following the procedure described by Albarella et al., *Nucleic Acids Res.*, 17(1):4293(1989). Alkyl carboxylic acids of different chain lengths between 2 and 10 are purchased from Fisher Scientific. They are activated with dicyclohexylcarbodiimide in dimethyl formamide as solvent. The activated carboxylic acids are then reacted with AMA to produce angelicin derivatives of different molecular weights.

EXAMPLE 2

Synthesis of Signature Compounds for Fluorescence Analysis

Instead of carboxylic acids, isothiocyanate derivatives of different flurophores are used to couple to AMA to produce compounds of well defined fluorescence characteristics like fluorescein, rhodamine, acridine etc.

EXAMPLE 3

Signature Compounds Introduced Directly to DNA

Following the procedure described by Miller et al., *Bioconjug. Chem.*, 3(1):74 (1992), alkylamines of different chain lengths are introduced to DNA by transamination of deoxycytidine residues. All compounds described in U.S. Pat. Nos. 6,187,566, 4,734,454, and 5,026,840 by Dattagupta et al. can be used in the present invention.

EXAMPLE 4

Multiple Sample Analysis by Mass Spectrometry

Compounds of example 1 are used to label 10 different DNA samples suspected of having defective globin gene representative of sickle cell anemia. The labeling is carried out by mixing 1 microgram of human genomic DNA with 0.1 microgram of the compound in 1 ml solution of a 10 mM borate buffer (pH 8.1) and the mixture is irradiated at 340±30 nm light for 60 minutes. After irradiation, samples are hybridized together to two sets of immobilized probes. One for normal and the other for sickle globin gene probe (Rabin et al., *Human Gen.*, 75:120 (1987)). After the hybridization and washing step(s), mass spectrometric analysis is conducted to determine which sample has normal and which sample has sickle globin gene.

EXAMPLE 5

Luminescence Analysis of Multiple Samples After Hybridization

Compounds of Example 2 are used in example 4 instead of compounds of example 1. After hybridization different flurophores are monitored in a spectrofluorometer.

The above examples are included for illustrative purposes only and are not intended to limit the scope of the invention. Many variations to those described above are possible. Since modifications and variations to the examples described above will be apparent to those of skill in this art, it is intended that this invention be limited only by the scope of the appended claims.

What is claimed is:

1. A method for analyzing nucleic acids in a plurality of samples, which method comprises:
   a) attaching each of target nucleic acids, if there is one in a sample, in a plurality of samples with a signature label separately whereby said target nucleic acid in each of said plurality of samples is attached to a detectably different signature label;
   b) pooling said labeled target nucleic acids in different samples into a single mixture;
   c) hybridizing each of said labeled target nucleic acids in said single mixture with a probe that is hybridizable to each of said labeled target nucleic acids in a single reaction to form a plurality of target nucleic acid/probe duplexes; and
   d) determining presence or absence, amount and/or identity of said target nucleic acid in each of said plurality of samples by analyzing presence or absence, amount and/or identity of said signature label in each of said target nucleic acid/probe duplexes.

2. The method of claim 1, wherein the labels are selected from the group consisting of a mass group, a metal, a fluorescent group, a luminescent group, a chemiluminescent group, an optical group, a charge group, a polar group, a color, a hapten, an antibody, an epitope-containing compound, a protein binding ligand, a nucleotide sequence, a radioactive group, an enzyme, an enzyme substrate, a particulate particle, magnetically responsive compound and a combination thereof.

3. The method of claim 1, wherein the labels are same kind or different kinds of substances.

4. The method of claim 1, wherein the labels are composites made of a plurality of substances and the labels are different from each other because they contain different kinds of substances having different chemical or physical composition or properties and/or contain same kinds of substances at different ratios.

5. The method of claim 1, wherein at least one of the samples is a biological, an agricultural, an veterinary, an environmental, or a human sample.

6. The method of claim 5, wherein the biological sample is a clinical sample.

7. The method of claim 1, wherein at least one of the target nucleic acids is a nucleic acid amplification product.

8. The method of claim 1, wherein the labels are attached to the target nucleic acids covalently or non-covalently.

9. The method of claim 1, wherein the labels are attached to the target nucleic acids directly or indirectly via a linker.

10. The method of claim 1, wherein the labels are attached to the target nucleic acids via a cleavable linkage or linker.

11. The method of claim 10, wherein the linkage or linker is cleavable via a physical, a chemical or an enzymatic treatment.

12. The method of claim 1, wherein the probe is immobilized on a surface and the target nucleic acids and the probe are hybridized on said surface.

13. The method of claim 12, wherein the probe is immobilized in a plurality of areas on the surface.

14. The method of claim 1, wherein the target nucleic acids and the probe are hybridized in a liquid.

15. The method of claim 14, wherein the hybridization is conducted in a liquid container selected from the group consisting of a beaker, a flask, a cylinder, a test tube, an eppendorf tube, a centrifugation tube, a culture dish and a multiwell plate.

16. The method of claim 1, wherein the pooling step is conducted prior to or concurrently with the hybridizing step.

17. The method of claim 1, wherein the pooling step is conducted after the hybridizing step but prior to or concurrently with the determining step.

18. The method of claim 1, wherein at least one of the signature labels is contained in a composition comprising said signature label and a binding ligand that facilitates attachment of said signature label to a target nucleic acid.

19. The method of claim 18, wherein the binding ligand comprises a chemical moiety that binds to a target nucleic acid and that, when activated by light, forms at least one covalent bond with the target nucleic acid.

20. The method of claim 19, wherein the binding ligand is an intercalator.

21. The method of claim 20, wherein the intercalator is a furocoumarin, a phenanthridine, a monoadduct forming compound or an angelicin derivative.

22. The method of claim 19, wherein the binding ligand is a non-intercalator.

23. The method of claim 22, wherein the non-intercalator is selected from the group consisting of a benzimide, a netropsin and a distamycin.

24. The method of claim 19, wherein the binding ligand is a photoreactive binding ligand.

25. The method of claim 18, wherein the composition further comprises a binding enhancer that has a specific affinity for nucleic acids.

26. The method of claim 25, wherein the binding enhancer is an intercalator or a non-intercalator.

27. The method of claim 26, wherein the intercalator is a monoadduct forming compound.

28. The method of claim 26, wherein the non-intercalator is selected from the group consisting of an oligo pyrrole, a phenyl indole, a nucleic acid and a protein.

29. The method of claim 25, wherein the binding enhancer has an affinity for nucleic acids equal to or greater than $1 \times 10^4$ mole$^{-1}$, specifically binds to nucleic acids in the presence of greater than 10 mM magnesium or comprises a nucleotide sequence that specifically binds to a target nucleic acid to be analyzed.

30. The method of claim 1, further comprising a step of releasing target nucleic acids from a sample source.

31. The method of claim 30, wherein the target nucleic acids are released and labeled concurrently using a composition comprising a signature label and a lysing agent for releasing nucleic acids.

32. The method of claim 25, wherein both the binding ligand and the binding enhancer are intercalator moieties and wherein at least one of said intercalator moieties forms at least one covalent bond with a nucleic acid to be analyzed.

33. The method of claim 25, wherein the composition further comprises a lysing reagent for releasing a target nucleic acid to be analyzed.

34. The method of claim 25, wherein the binding ligand, binding enhancer and signature label in at least one of the compositions are bound together in the form of a covalent or noncovalent complex.

35. The method of claim 34, wherein the signature label is linked to the binding ligand and/or binding enhancer in the complex directly or indirectly via a linker.

36. The method of claim 34, wherein the signature label is linked to the binding ligand and/or binding enhancer in the complex via a cleavable linkage or linker.

37. The method of claim 36, wherein the linkage or linker is cleavable via a physical, a chemical or an enzymatic treatment.

38. The method of claim 1, wherein the labeled target nucleic acids are hybridized to a plurality of probes and each of said probes hybridizes to a different kind of target nucleic acid.

39. The method of claim 38, wherein the labeled target nucleic acids are hybridized to the plurality of probes simultaneously.

40. The method of claim 1, wherein the labeled target nucleic acids comprising DNA, RNA, PNA or a combination thereof.

41. The method of claim 2, wherein the chemiluminescent group is an acridinium ester.

* * * * *